United States Patent
Neumüller

(10) Patent No.: US 6,555,336 B1
(45) Date of Patent: Apr. 29, 2003

(54) METHOD FOR PREPARING ALBUMIN HYDROLYSATES

(76) Inventor: Waldemar Neumüller, Wilhelm-Baum-Weg 29, D-37077 Göttingen (DE)

(*) Notice: Subject to any disclaimer, the term of this patent is extended or adjusted under 35 U.S.C. 154(b) by 0 days.

(21) Appl. No.: 09/914,022

(22) PCT Filed: Feb. 23, 2000

(86) PCT No.: PCT/EP00/01484

§ 371 (c)(1), (2), (4) Date: Aug. 20, 2001

(87) PCT Pub. No.: WO00/49886

PCT Pub. Date: Aug. 31, 2000

(30) Foreign Application Priority Data

Feb. 23, 1999 (DE) .......................... 199 07 726

(51) Int. Cl.⁷ ........................ C12P 21/06; C12Q 1/46; A21D 2/00; A23C 21/00; A23B 7/10
(52) U.S. Cl. ..................... 435/68.1; 426/7; 426/20; 426/32; 426/49
(58) Field of Search ................ 435/68.1; 426/7, 426/20, 32, 49

(56) References Cited

U.S. PATENT DOCUMENTS 3,857,966 A * 12/1974 Feldman et al.
4,482,574 A   11/1984 Lee .............................. 426/7
5,726,033 A    3/1998 Neumüller ............... 435/68.1

OTHER PUBLICATIONS

Notification of Transmittal of Copies of Translation of the International Preliminarhy Examination Report, 1 page, Sep. 10, 2001.
International Preliminary Examination Report, 5 pages, Nov. 14, 2000.

* cited by examiner

Primary Examiner—Christopher R. Tate
Assistant Examiner—Randall Winston
(74) Attorney, Agent, or Firm—Thomas, Kayden, Horstemeyer & Risley

(57) ABSTRACT

In a method for preparing albumin hydrolysates from a starting material containing albumins in concentrated or isolated form, the starting material are homogenized with an aqueous solution at a temperature of between 10 and 80° C. and at a pH of between 8 and 12 in the presence of a first protease for the enzymatic hydrolysis of the albumins. At least one further protease whose cleaving spectrum differs from that of the first protease is added after between 1 and 60 min. from the start of homogenization for the further enzymatic hydrolysis of the albumins. The proteases are inactivated by a heat treatment at a pH below 7.5 within between 1 and 60 minutes from addition of the last protease. The non-hydrolyzed albumins are precipitated at a pH below 7.5. The precipitated non-hydrolyzed albumins are separated from the albumin hydrolysates contained in the solution; and the albumin hydrolysates contained in the solution are concentrated.

10 Claims, No Drawings

METHOD FOR PREPARING ALBUMIN HYDROLYSATES

FIELD OF THE INVENTION

The invention relates to a method for preparing albumin hydrolysates from a starting material containing albumin in concentrated of isolated form.

BACKGROUND OF THE INVENTION

Albumin hydrolysates are albumin fragments of different lengths, which may be produced by chemical hydrolysis by means of alkali or acid or by enzymatic hydrolysis. In the chemical hydrolysis protein damages like lysinoalanine and chloropropanol may occur as a drawback. Known disadvantages of the enzymatic hydrolysis are long hydrolysis times and bitter peptides. Further, the albumin yield in relation to the albumin input is clearly smaller with enzymatic hydrolysis than with chemical hydrolysis. On the other hand, the chemical hydrolysis takes place more or less non-specifically. In weighing up all factors, the enzymatic hydrolysis is presently preferred for preparing albumin hydrolysates for the food and pharmaceutics sectors.

Prior art methods for preparing albumin hydrolysates from a starting material containing albumin in concentrated or isolated form by means of enzymatic hydrolysis generally have a similar structure, the albumin, as a rule being dissolved before or after the enzymatic hydrolysis at an alkaline pH.

It is known from U.S. Pat. No. 1,231,652, for example, to carry out an enzymatic hydrolysis at the isoelectric point of the albumin with acid proteases being active within this pH-range for reducing the viscosity of albumin dispersions. Afterwards the pH is raised, sometimes up to 11.8, by means of alkali, and the albumins are alkalinally hydrolysed for 1 to 2 hour at temperatures of 50 to 85° C. By means of this, the albumins are dissolved, and are then further cleaved by means of the protease pepsin within a high acid pH-range. It is a drawback of this known method that a strong formation of salt is associated with the frequently changing pH of the albumin containing dispersion or solution, and that the enzymatic hydrolysis is only carried out within the acid pH range, in which hydrolysis times of more than 20 hours are necessary to obtain an acceptable albumin hydrolysate yield.

From U.S. Pat. No. 4,473,589 it is known to combine an enzymatic hydrolysis with an alkaline hydrolysis. To this end, it is at first alkalinally hydrolysed under strongly alkaline conditions at a pH of over 12, and then the albumin dispersion is further liquefied by means of an alkaline protease. The temperatures of the alkaline hydrolysis over 1 to 2 hours are between 50 to 80° C., and the temperatures of the enzymatic hydrolysis are between 40 to 60° C. The time of the enzymatic hydrolysis is up to 48 hours. Like the method according to U.S. Pat. No. 1,231,652 described above, the method according to U.S. Pat. No. 5,473,589 results into considerable alkali damages of the obtained albumin hydrolysates because of the high temperatures and of the high pH applied simultaneously. This strongly limits a use of the obtained albumin hydrolysates in the food and pharmaceutics sector. Additionally, especially the long hydrolysis times in the method according to U.S. Pat. No. 4,473,589 are unsuitable for an economic preparation of albumin hydrolysates at a large scale.

A method for preparing a soya albumin hydrolysate is known from EP 0 199 981 A2. Here, a neutral protease is used at a neutral pH. To support the effect of this neutral protease, a fine dispersion of the starting material is initially prepared in that the starting material is homogenized at 60 to 100° C. over a pressure drop of 100 to 800 bars so that the starting material is present with a low particle size and thus a great engageable surface. Depending of the wanted solubility of the desired product, it is then hydrolysed for a period of 5 to 180 min. The resulting dispersion is dried after inactivation of the used enzymes without further processing. It is one of the drawbacks of this known method that a dispersion of different albumin fragments up to non-processed albumins is obtained. Further, the availability of neutral proteases is limited. Additionally, the high pressures and the simultaneous high temperatures during the homogenization lead to a strong protein denaturation so that as a result the possibilities of engagement by the protease are strongly limited which increases the hydrolysis time. All at all, the obtained albumin hydrolysates are limited to a small number of fields of application.

A method for preparing albumin hydrolysates from a starting material containing albumin in a concentrated or isolated form is known from EP 0 298 419 A2, which method is closest to the present invention of all present prior art. In this known method, vegetable albumins are hydrolysed over 10 to 60 min. chemically by acid or alkali at 60 to 180° and/or enzymatically and/or by means of reducing or oxidizing agents. The kind and the way of hydrolysis shall be selected based on the application of the albumin hydrolysis to be prepared. A clear concept for the preparation of albumin hydrolysates does appear from EP 0 298 419. Instead, all known working mechanisms are simply listed.

The preparation of functional disperse as well as of fully soluble albumin hydrolysates is described in EP 0 480 104 A1. Here, the positive effect of a high alkaline pH of 9 to 11 is emphasized. It is particularly pointed out that the toxic amino acid lysinoalanine, which is a measure of albumin damages, does not exceed a concentration of 300 ppm. The temperatures in the enzymatic hydrolyses are between 10 and 75° C., and they are not tuned to the different proteases used. The hydrolysis time is 10 to 240 min.

A special method for preparing rice albumin hydrolysates is disclosed in DE 195 02 167 C2. Here, a hydrolysis takes place in the present of adsorbents. The pH is between 8 and 10, the temperature is between 40 and 90° C., and the hydrolysis time is between 1 and 24 hours. Because of the multistage processing of the starting material using filtration by means of filter presses and processing with activated carbon, the known preparation method is very cost intensive. It is also a particular drawback that the conserved albumin hydrolysate solution can only be processed after a maturation time of 14 days and after a repeated application of activated carbon. Thus, a preparation of albumin hydrolysates at low cost is not possible.

From DE 33 06 009 C2 it is known to use enzymes on a fixed support for the hydrolysis of albumins. The main emphasis is on fungal proteases. The pH at which the hydrolysis takes place is between 6 and 9. The hydrolysis time is adjusted to values between 10 and 100 min. by means of the flow velocity along the fixed support. At the end, the high cost of coupling the enzymes to the support material, the disposal of the support material and the difficulties with a technical layout stand against a commercial application of this known method.

It is common to all of the above described prior art methods, except of EP 0 199 981 A2, that, after the hydrolysis, the enzymes are heat inactivated and the non-hydrolysed albumin parts are separated from the albumins hydrolysed from the starting material by precipitation at the isoelectric point of the non-hydrolysed albumin parts to obtain a albumin hydrolysate solution as pure as possible.

Inter alia from Ullmanns Encyclopaedia of technical Chemistry, Vol. 10, page 494 (1975) it is known that the activity of enzymes is considerably reduced as an effect of thermal, enzymatic-proteolytic and mechanical stress during a step of homogenization, particularly by high pressure disintegration.

The invention is based on the problem to provide a method for preparing albumin hydrolysates from a starting material containing albumins in a concentrated or isolated form which may by applied in a continuous and thus economic form because of a short hydrolysis time and which, with a great flexibility with regard to the starting material and the albumin hydrolysates to be prepared, results into method product with a low bitter content.

SUMMARY OF THE INVENTION

The invention discloses a method for preparing albumin hydrolysates from a starting material containing albumins in concentrated or isolated form, the, method comprising the steps of homogenizing the starting material with an aqueous solution at a temperature of between 10 and 80° C. and at a pH of between 8 and 12 in the presence of a first protease for the enzymatic hydrolysis of the albumins; adding at least one further protease whose cleaving spectrum differs from that of the first protease after between 1 and 60 min. from the start of homogenization for the further enzymatic hydrolysis of the albumins; inactivating the proteases by a heat treatment at a pH below 7.5 within between 1 and 60 minutes from addition of the last protease; precipitating the non-hydrolysed albumins at a pH below 7.5; separating the precipitated non-hydrolysed albumins from the albumin hydrolysates contained in the solution; and concentrating the albumin hydrolysates contained in the solution.

Preferably, in the step of adding the at least one further protease, the further protease is added within between 5 and 15 minutes from the start of homogenization.

Preferably, in the step of adding the at least one further protease, at least two further proteases are added after between 1 and 60 minutes from the start of homogenization, which further proteases differ from each other with regard to their cleaving spectrum.

Preferably, the full period from the start of homogenization up to the inactivation of the proteases is no longer than 60 minutes.

Preferably, in the step of homogenizing the starting material with an aqueous solution, the pH of between 8 and 12 is adjusted with an alkaline agent selected from the group consisting of alkaline hydroxides, alkaline earth hydroxides, alkaline carbonates, and alkaline earth carbonates.

Preferably, in the step of homogenizing the starting material with an aqueous solution, the homogenization is effected by a one time high pressure disintegration of the albumin isolate in an aqueous solution with a drop in pressure of between 5 and 100 MPa.

Preferably, in the step of homogenizing the starting material with an aqueous solution, the first protease in whose presence the homogenization takes place is used with a concentration by weight of less than 1% as related to the albumin isolate.

Preferably, in the steps of precipitating the non-hydrolysed albumins at a pH below 7.5 the non-hydrolysed albumins being precipitated at the isoelectric point of the non-hydrolysed albumins.

Further, the method preferably comprises the further step of adding a protease to the concentrated solution again.

Further, the method preferably comprises the further step of, for a certain interval of time, increasing the pH of the concentrated solution to between 11 and 13 and its temperature to between 25 and 35° C.

In the new method, the pH of the albumin containing starting material is initially adjusted to 8 to 12, preferably to 9 to 10, by using alkaline or alkaline earth hydroxides or carbonates. Then, this suspension is homogenized at a temperature of below 80° C., particularly at 40° C., in the presence of a first protease. The homogenization can be carried out by means of all common techniques of homogenization. A homogenization by means of high-pressure disintegration over a pressure drop of 50 to 1000 bars, alone or in combination with other techniques of homogenization, is particularly preferred. The first protease can be added to the suspension directly before the homogenization or already at a certain interval of time before that. After 1 to 90 min. from the start of the homogenization at least one further protease is added to the dispersion of the starting material, the maximum activity of which within the pH range mentioned above is at least 50%. While homogenizing, the hydrolysis time after adding the latter protease is 60 min. at maximum, particularly 10 to 15 min., no pH-correction being preferably made during the hydrolysis time. After that, the used enzymes are inactivated by heat treatment at a pH below 7.5, particularly below 6.5. All proteases except of acid proteases are suitable for the enzymatic hydrolysis carried out in this way.

To obtain soluble pH-stable albumin hydrolysates, the pH is then adjusted to the isoelectric point of the non-hydrolysed albumins. This point is particularly within a pH-range of 4.2 to 4.5. The dispersion resulting at the isoelectric point is separated into solid matter and solution, for example, by means of centrifugation under vacuum or membrane filtration while avoiding foam formation. The desired albumin hydrolysates are within the solution. After adjusting a desired pH of the solution, the solution may be further divided up for different molecular weights by means of membrane filtration. Afterwards, a concentration takes place, generally by drying.

It has to be regarded as surprising that despite the negative effects of the homogenization on the activity of the first protease the homogenization enhances the enzymatic (partial) disintegration by means of the first protease to a considerable extend so that the new method shows very short processing times as compared to other methods. This may be put down to the possibilities of attack by the enzymatic dissociation by the first proteases being over-proportionally increased by the homogenization. Thus, the enzymatic hydrolysis under homogenization of the starting material at a pH of over 8 accelerates the desired hydrolysis of the proteins very considerably. Herein, it is possible to at first pre-cleave with a protease and to further cleave with the second protease. If no high pressure disintegration is used as a homogenization technique, an intensive homogenization has to be ensured by another kind of homogenization like, for example, ultrasound, colloid mills, rotor-stator system or homogenizing stirrers. In this case, a homogenization for at least 15 min. is recommended even before adding the first protease.

If bitter components from the hydrolysis of the albumin containing starting material occur in the method described up to here, these bitter components may be reduced in that a centrifugation under vacuum at a pH of about 6.5 is carried out before the heat treatment of the proteases, and in that the obtained solution is concentrated and then subjected to a plasteine reaction during which the pH is adjusted to 11 to 13 at a temperature of below 35° C. by means of alkaline or alkaline earth hydroxides. The alkaline solution is then intensively stirred at the mentioned pH for 5 to 30 min. Then, the pH is adjusted to 4.2 to 7.5, and the enzymes in the solution are inactivated by heat treatment as described above, and the albumin hydrolysates are concentrated by drying, which may be done after a prior separation for different molecular weights, if desired.

The albumin hydrolysates obtained from the new method show a high functionality and a full solubility depending of their degree of hydrolysis. Functional albumin hydrolysates can be produced without significant losses, soluble hydrolysates can be produced with yields of 60 to 80% within a few minutes. There is no limitation to a special raw material as a starting material.

PREFERRED EMBODIMENTS OF THE INVENTION

In the following, the invention will be further explained and described by means of examples.

1. Soluble Soya Albumin Hydrolysate 1 kg soya albumin isolate is mixed and homogenized over 15 min. with 6.5 kg 50° C. warm water. Then, the pH is raised to 10.5 by a 25% solution of calcium hydroxide in water, and 0.2% by weight of a neutral protease are added. Here, the weight of the protease is related to the weight of the albumin input. The obtained dispersion is homogenized for 15 min. During this, the temperature of the dispersion slightly increases; the pH decreases to 9.5. Under continuous homogenization, at first 1 to 1.5% by weight of an alkaline protease are added, the concentration being again defined in relation to the weight of the albumin input and the concentration being to be tuned to the respective starting material so that the pH of the dispersion decreases to 7 to 7.5 within about 7 min. After these about 7 min., the pH is adjusted to 8.2 by further calcium hydroxide, and a neutral protease is added with a concentration of 1% by weight. After 15 min. of homogenization the pH of the dispersion is 7.2. Then, the dispersion is adjusted to pH 6 by 15% sulphuric acid and afterwards heated up to 110° C. for 60 sec. After cooling down to 50° C., the pH is adjusted to 4.5 by sulphuric acid, and the dispersion is centrifuged at 6000×g under vacuum. The supernatant containing the hydrolysed albumins can be spray dried, directly or after neutralization. The supernatant is fully soluble and free of solid matter.

2. Soluble, Clear and Bitter-free Soya Albumin Hydrolysate 1 kg soya albumin isolate is added to and well mixed with 6.5 kg 40° C. warm water. Then, the pH is raised to 10.5 by a 25% solution of sodium hydroxide in water, while at the same time 0.25% by weight of an alkaline protease are added, the percentage by weight of the alkaline protease being related to the weight of the albumin input. The resulting dispersion is stirred for 5 min. and then a homogenized via a pressure drop of 300 bar. The temperature of the dispersion rises up to 45° C.; the pH decreases to 9.0. Afterwards, a second alkaline protease is added with a concentration of 1.5% by weight as related to the albumin input under insensitive stirring. The second alkaline protease is selected in such a way that it has a different cleaving spectrum than the first protease. After 7 min., the pH of the dispersion is 7, and it is adjusted to 8.2 by further sodium hydroxide. Afterwards, 1.5% by weight of a neutral protease are added, and it is further hydrolysed for 8 min. The pH decreases to 6.5. The resulting suspension is centrifugated at 6000×g. Afterwards, the resulting supernatant is heated up to 110° C. for 60 sec., and then concentrated up to 30% solid matter content in a vacuum. After cooling down to 30° C., further 0.5% by weight of the last protease are added, and the pH is adjusted to 12 while stirring. The resulting alkaline solution is intensively stirred for 15 min., without foam being produced. Then, the pH of the solution is adjusted to 4.5 by means of hydrochloric acid, and afterwards the solution is for a second time heated up to 110° C. for 60 sec., The non-hydrolysed albumins which are precipitated here are separated by centrifugating at 50° C. and 6000×g and filtering by micro filtration at a pore size of 0.2 $\mu$m. After neutralization the supernatant or the permeate can be directly spray dried. The obtained albumin hydrolysate is fully soluble, clear and free of bitter peptides.

3. Soluble and Clear Wheat Albumin Hydrolysate without Bitter Peptides 1 kg vital gluten is homogenized in 7 kg of 40° C. warm water to which calcium hydroxide is added to such an extend that the pH is 10.5. This pH is kept constant during the addition of the albumin containing starting material. 1.5% by weight of an alkaline protease as related to the weight of the albumin input are added to the obtained dispersion. After 15 min., the pH is 7.5, and it is adjusted to 8.2 by calcium hydroxide. Afterwards, a second alkaline protease having another cleaving spectrum than the first protease is added with a concentration of 1.5% by weight. After further 15 min., the pH is 7.2. The dispersion is reduced to pH 6 by hydrochloric acid, and centrifugated under vacuum at 6000× g. The cleared liquid phase is then added with hydrochloric acid again so that the pH is 4.2, and then heated up to 110° C. for 60 sec. After cooling down to 50° C., it is again centrifugated under vacuum. The obtained supernatant is fully soluble, clear and free of bitter petides. It can be directly concentrated, particularly dried.

4. Soluble Fish Protein 1 kg purified fish protein is taken up in 7 kg of 50° C. warm water while homogenizing by means of a rotor-stator-system (Ultraturrax). Sodium hydroxide is added so that a pH of 11.2 is reached. Directly after reaching this pH, 2% by weight of an alkaline protease as related to the protein content of the starting material are added to this dispersion. Under strong homogenization the pH decreases to 9 within 10 min. Without interrupting the homogenization a second alkaline protease is added which differs from the first protease with regard to the cleaving spectrum. Its activity is selected so that the pH reaches 7.2 within 20 min.

This dispersion is centrifugated under vacuum at 6000×g, and the cleared phase is adjusted to pH 4.2 by hydrochloric acid. Afterwards, this solution is heated up to 110° C. for 60 seconds, and directly afterwards cooled down to 50° C. and again centrifuged under vacuum at 6000×g. The solution obtained in this way can either be dried or further purified by means of filtration.

What I claim is:

1. A method for preparing albumin hydrolysates from a starting material containing albumins in concentrated or isolated form, the method comprising the steps of:

homogenizing the starting material with an aqueous solution at a temperature of between 10 and 80° C. and at a pH of between 8 and 12 in the presence of a first protease for the enzymatic hydrolysis of the albumins;

adding at least one further protease whose cleaving spectrum differs from that of the first protease after between 1 and 60 min. from the start of homogenization for the further enzymatic hydrolysis of the albumins;

inactivating the proteases by a heat treatment at a pH below 7.5 within between 1 and 60 minutes from addition of the last protease;

precipitating the non-hydrolysed albumins at a pH below 7.5;

separating the precipitated non-hydrolysed albumins from the albumin hydrolysates contained in the solution; and concentrating the albumin hydrolysates contained in the solution.

2. The method of claim 1, wherein, in the step of adding the at least one further protease, the further protease is added within between 5 and 15 minutes from the start of homogenization.

3. The method of claim 1, wherein, in the step of adding the at least one further protease, at least two further proteases are added after between 1 and 60 minutes from the start of homogenization, which further proteases differ from each other with regard to their cleaving spectrum.

4. The method of claim 1, wherein the full period from the start of homogenization up to the inactivation of the proteases is no longer than 60 minutes.

5. The method of claim 1, wherein, in the step of homogenizing the starting material with an aqueous solution, the pH of between 8 and 12 is adjusted with an alkaline agent selected from the group consisting of alkaline hydroxides, alkaline earth hydroxides, alkaline carbonates, and alkaline earth carbonates.

6. The method of claim 1, wherein, in the step of homogenizing the starting material with an aqueous solution, the homogenization is effected by a one time high pressure disintegration of the albumin isolate in an aqueous solution with a drop in pressure of between 5 and 100 MPa.

7. The method of claim 1, wherein, in the step of homogenizing the starting material with an aqueous solution, the first protease in whose presence the homogenization takes place is used with a concentration by weight of less than 1% as related to the albumin isolate.

8. The method of claim 1, wherein, in the steps of precipitating the non-hydrolysed albumins at a pH below 7.5 the non-hydrolysed albumins are being precipitated at the isoelectric point of the non-hydrolysed albumins.

9. The method of claim 1 and comprising the further step of adding a protease to the concentrated solution again.

10. The method of claim 1 and comprising the further step of, for a certain interval of time, increasing the pH of the concentrated solution to between 11 and 13 and its temperature to between 25 and 35° C.

* * * * *